United States Patent [19]

Furutani et al.

[11] Patent Number: 4,824,782

[45] Date of Patent: Apr. 25, 1989

[54] DNA BASE SEQUENCE, METHOD FOR PREPARING A RECOMBINANT PLASMID INCLUDING THE DNA BASE SEQUENCE, AND BREEDING METHOD FOR ENHANCING THE PROTEIN-SECRETING ABILITY OF A MICROORGANISM BY INTRODUCING THEREINTO THE RECOMBINANT PLASMID

[75] Inventors: Yoshio Furutani, Miuragun; Noboru Tomioka, Mobara; Masaru Honjo, Mobara; Kazuaki Manabe, Mobara; Hiroaki Shimada, Mobara, all of Japan

[73] Assignees: Agency of Industrial Science and Technology; Ministry of International Trade and Industry, both of Japan

[21] Appl. No.: 180,691

[22] Filed: Apr. 8, 1988

Related U.S. Application Data

[63] Continuation of Ser. No. 649,278, Sep. 11, 1984, abandoned.

[30] Foreign Application Priority Data

Sep. 12, 1983 [JP] Japan ............................. 58-166665

[51] Int. Cl.$^4$ ...................... C12N 15/00; C12N 1/20; C12N 7/00; C12P 21/00
[52] U.S. Cl. ................................ 435/172.3; 435/68; 435/91; 435/317.1; 435/320; 435/243; 435/252.31; 435/252.33; 935/29; 935/38; 935/74; 536/27

[58] Field of Search ................... 435/68, 70, 243, 253, 435/320, 317.1, 91; 536/27; 935/29, 38, 56, 80, 74

[56] References Cited

PUBLICATIONS

Chang et al. (1982) NSC Symp. Ser. 4:254–262, abst (CA100 46295).
Palva et al. (1981) Gene 15: 43–51.
Proc. Nat'l Acad. Sci. USA 74, (1977), pp. 560–564.
J. Mo. Biol., 3, (1961), pp. 208 to 218.
Mol. Gen. Genet., 168, (1979), pp. 111 to 115.
Nucleic Acid Res., 7, (1979), pp. 1513 to 1523.
J. Biochem., 45, (1958), pp. 185–194.

*Primary Examiner*—Thomas G. Wiseman
*Assistant Examiner*—Stephanie Seidman
*Attorney, Agent, or Firm*—Fisher, Christen & Sabol

[57] ABSTRACT

This invention relates to a DNA base sequence, capable of increasing the amount of protein secreted by microorganisms, and its derivative sequences; a recombinant plasmid including the whole or a part of said DNA base sequence; a method for preparing the recombinant plasmid in which, when microorganisms having introduced thereinto a recombinant DNA including the desired DNA base sequence are to be separated in the process of cloning, suitable transformants can be efficiently selected by taking the amount of protein secreted out of the cells and particularly the activity of an enzyme protein as an index; and a method of microbial breeding which comprises introducing the recombinant plasmid into a microorganism to increase the amount of protein secreted by the microorganism.

7 Claims, 4 Drawing Sheets

◀ ClaI site  Partial digestion
◁ EcoRI site  Ligation

◀ ClaI site
◁ EcoRI site

FIG. 4

5'
TCTCTT `TTGAAA` TTGCGACGTCAGGGAC `TATAGT` CCTTAGCGG ---
      -35                      TATA
           16 b

~400b

```
         AA
       T G  A
      T-A  G-C
      A-T  T-A
      A-T  C-G
      C-G  A-T
      T-A  G-C
      C-T  A-T
      T-A  A-T
      A-T  A-T
      A-T  A-T
CTCGAT         CTT TTGTGCATTTTTCACCC
                                    3'
```

DNA BASE SEQUENCE, METHOD FOR PREPARING A RECOMBINANT PLASMID INCLUDING THE DNA BASE SEQUENCE, AND BREEDING METHOD FOR ENHANCING THE PROTEIN-SECRETING ABILITY OF A MICROORGANISM BY INTRODUCING THEREINTO THE RECOMBINANT PLASMID

This application is a continuation of application Ser. No. 649,278, filed Sept. 11, 1984 and now abandoned.

BACKGROUND OF THE INVENTION

1. Field of the Invention

This invention relates to a DNA base sequence capable of increasing the amount of protein secreted by microorganisms and its derivative sequences; a recombinant plasmid including the whole or a part of said DNA base sequence; a method for preparing the recombinant plasmid; and a method of microbial breeding which comprises introducing the recombinant plasmid into a microorganism to increase the amount of protein secreted by the microorganism.

2. Description of the Prior Art

Some microorganisms (e.g., bacteria, yeasts and the like) secrete protein into the periplasm or out of the cells. Among others, bacteria of the genus Bacillus secrete a large amount of protein out of the cells.

From the viewpoint of microbial production of protein, it is of great significance to incorporate the genetic information involved in the promotion of protein secretion by such microorganisms into a host vector system according to genetic engineering techniques and thereby create a host vector system having the genetic information involved in the promotion of protein secretion. That is, the gene associated with high amounts of protein secretions can be expressed by forming such a host vector system within a microorganism. If the microorganism having amounts of protein secretions ability imparted thereto is grown, for example, in a culture medium, a large amount of protein is secreted into the culture medium. This protein can then be recovered from the culture medium according to a simple procedure.

SUMMARY OF THE INVENTION

It is an object of the present invention to provide a DNA base sequence, capable of increasing the amount of protein secreted by microorganisms, and its derivative sequences.

It is another object of the present invention to provide a recombinant plasmid including the whole or a part of said base sequence and an efficient method for preparing this recombinant plasmid.

It is still another object of the present invention to provide a method of microbial breeding for increasing the amount of protein secreted by a microorganism by introducing thereinto such a recombinant plasmid.

These objects of the present invention are accomplished by (a) a DNA base sequence capable of increasing the amount of protein secreted in which one of the strand comprises bases arranged in the following order:

| ATCGA | TACGC | TTCTC | CAGAG |
|-------|-------|-------|-------|
| AGAGC | TTGAG | GACAT | AGTCA |
| AAGAA | CTGCC | TTTAA | TTGAT |

-continued

| GAAGT | CGGAC | AGGCG | CTGCT |
|-------|-------|-------|-------|
| CGGTT | ATGAA | AACGA | TTATT |
| ACATG | ATGCT | CGGGC | TCGTC |
| AAAGC | CATTG | AATGC | AACAA |
| CTGGG | ACTGT | GACGA | GTGGG |
| GAAAA | GAACT | GGACA | AAGAA |
| GAAGC | ATATG | AATGT | TACTT |
| ACAGG | CGATC | GAATG | GTGCC |
| GGCAG | CTTAT | CGTGA | ATTGA |
| GGCGC | TTTAA | GCCGA | CCACC |
| TGAGG | GCGAT | GATGA | ACCGG |
| CTTTG | CTCTC | TGAAC | AGACT |
| GACAC | GGATG | CCGTC | GGGAT |
| TAAAT | GTCAC | ATCAA | AATCA |
| TTTTT | GATGC | CGGTC | TGCTT |
| AATGA | GCCGC | TTGAC | CGCCG |
| CGGCG | TCAGA | TGATT | GCGCT |
| GCGGT | GAGGA | TGCGG | CGCGC |
| AAGCT | CTTTT | GACGC | CGACA |
| GCCGC | GCAAG | GAGCA | GACGG |
| GCGTC | CTCCA | GCATG | CCCGC |
| AGCCT | CTTTT | GCGGA | CGCTG |
| TCAAA | ATATC | TGCGT | GAATC |
| GTGGG | AGCAG | GCGCA | GGATT |
| GCGTA | TGGCG | CGGCG | AAAAC |
| AGGAC | AGCAT | GGATA | CACAT |
| AAAGC | ATGCG | GCGGC | CTCCT |
| TCTGA | GATAA | CATTC | GTTAT |
| ACATG | AGTAT | AGGCG | GCGTG |
| ATAAC | GAGTT | ATGAC | ATGCA |
| AAAAG | ACCAC | AATGC | GGGTG |
| TTGCG | GTCTT | TTCGG | TGTTT |
| GTCGG | TGGTT | ATGCG | ACGCT |
| GTTCG | CCCAT | TCTCT | TTTGA |
| AATTG | CGACG | TCAGG | GACTA |
| TAGTC | CTTAG | CGGTT | TGTCG |
| GAAAA | CCGTT | AAAAA | ACCAG |
| CAGAA | CCACC | AGATT | GATCT |
| GCTTC | ATCCC | AAACG | TCTGC |
| CTTTA | TGGTA | GTTAT | ATAGT |
| CCTGT | TCGCC | AAATG | CTCTG |
| TTCGG | GACTA | TGGGA | TTACC |
| GTGGT | TTGCG | GTGTC | ACGCA |
| GATAC | TTTTA | CACAT | ACTTT |
| TCGGT | GAAAA | ATCCC | GCAAA |
| AACGT | TTACA | CTATT | AGTAA |
| CAGAT | CAAAT | ACCTA | GGACT |
| CGTTC | ACCAT | ACACA | ATTCA |
| TTGAT | CTTTC | AAAAA | AAGGA |
| GTGTG | GAAAC | GGTGG | AAAAG |
| AAATT | AGAAG | AAGTA | AAGCA |
| ATTAT | TATTC | CGACT | TGAAA |
| ATGAT | ATCAG | AGAAA | CAACC |
| GACTC | ATTAC | GAAAC | ATTAA |
| CAAAA | GCATT | GATCA | GCTCG |
| ATAAA | TTCTC | ATATG | CAATG |
| AAAAT | TTCTT | AAAAA | GACTT |
| GGAAA | CAAGT | CTTTT | TTTTG |
| TGCAT | TTTTC | ACCCA | TTTCA |
| TGGAT | AAAGT | ATTAT | ACGAT |
| TGTTA | AAAAA | CGAAA | AACCT |
| GCTGT | CTTTC | ATCAC | CTGCA |
| TTTAG | TAAAA | TAGAA | TGGGA |
| GGGTG | AAGAC | AATTA | TTGAG |
| CAAAT | GTGTT | TAGAT | GCCGA |
| AACGA | TTAAA | GGGAA | GATGA |
| AGGAA | ATTGT | TGGGG | ATAAA |
| GTCGA | TAATC | TACAT | TTAGA |
| AGAGA | CTCTT | TTGAC | CTTCA |
| TTAAT | GAAAA | GAAGC | ACTTT |
| TCATT | CGGTG | TCCTT | GCTTT |
| CCAGC | ATTAT | GTTGC | TTTTA |
| AGGGT | ACACA | TTCCT | CGGAA |
| ATCAC | ACTAC | TGGCC | GCTGG |
| AATTG | AACTT | TTAAT | TTTAG |
| CTTTT | GATAT | TTTTG | ACGAT |
| ATTGA | AGATG | AAGAT | AACTT |
| TAATA | AGGCA | TGGAT | GCAAA |
| CTGAC | CATGC | TATAT | CCCTG |
| AATGC | GGCTA | CTTCT | CTGTA |
| TTCAA | TAAGC | CTGCA | AGCCA |
| TTTGT | GAGCT | TGAAT | CAAAC |

| | |
|---|---|
| AATCG | AT | where A, T, C and G represent adenine, thymine, cytosine and guanine, respectively, and derivative sequences thereof;

(b) a recombinant plasmid including the whole or a part of the aforesaid DNA base sequence or a derivative sequence thereof;

(c) a method for preparing the aforesaid recombinant plasmid in which, when microorganisms having introduced thereinto a recombinant DNA including the desired DNA base sequence are to be separated in the process of cloning, suitable transformants can be very efficiently selected by paying attention to an enzyme protein secreted out of the cells and determining the amount thereof and particularly the extracellular enzyme activity thereof to find transformants having markedly increased amounts of protein secretion; and (d) a method of microbial breeding which comprises introducing the aforesaid recombinant plasmid into a microorganism to increase the amount of protein secreted by the microorganism.

The phrase "enhancement of the protein-secreting ability of a microorganism" means an increasing of the level of a secreted protein from a microorganism and the phrase "separate coexistence" means of the DNA sequence and a gene encoding the secreted protein in the bacterium.

BRIEF DESCRIPTION OF THE DRAWINGS

FIG. 4 is a base sequence diagram showing the presence of RNA synthesis initiation sites and termination sites in the DNA base sequence of the present invention.

DETAILED DESCRIPTION OF THE PREFERRED EMBODIMENTS

Figure 1:
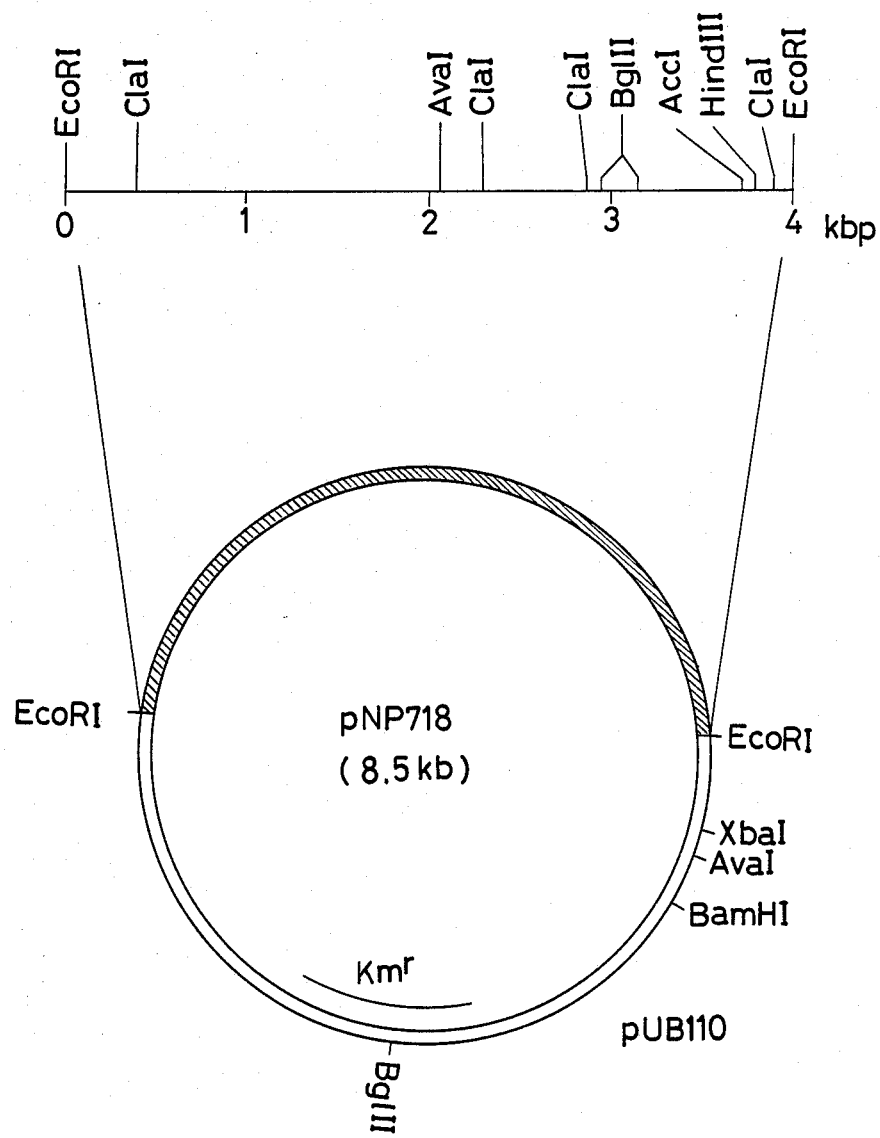
FIG. 1 is a restriction enzyme cleavage map of plasmid pNP718 in accordance with the present invention.

In accordance with the present invention, the DNA base sequence capable of increase the amount of protein secreted by microorganisms is one which defines, from the 5' to the 3' terminus, the following arrangement of bases:

| | | | |
|---|---|---|---|
| ATCGA | TACGC | TTCTC | CAGAG |
| AGAGC | TTGAG | GACAT | AGTCA |
| AAGAA | CTGCC | TTTAA | TTGAT |
| GAAGT | CGGAC | AGGCG | CTGCT |
| CGGTT | ATGAA | AACGA | TTATT |
| ACATG | ATGCT | CGGGC | TCGTC |
| AAAGC | CATTG | AATGC | AACAA |
| CTGGG | ACTGT | GACGA | GTGGG |
| GAAAA | GAACT | GGACA | AAGAA |
| GAAGC | ATATG | AATGT | TACTT |
| ACAGG | CGATC | GAATG | GTGCC |
| GGCAG | CTTAT | CGTGA | ATTGA |
| GGCGC | TTTAA | GCCGA | CCACC |
| TGAGG | GCGAT | GATGA | ACCGG |
| CTTTG | CTCTC | TGAAC | AGACT |
| GACAC | GGATG | CCGTC | GGGAT |
| TAAAT | GTCAC | ATCAA | AATCA |
| TTTTT | GATGC | CGGTC | TGCTT |
| AATGA | GCCGC | TTGAC | CGCCG |
| CGGCG | TCAGA | TGATT | GCGCT |
| GCGGT | GAGGA | TGCGG | CGCGC |
| AAGCT | CTTTT | GACGC | CGACA |
| GCCGC | GCAAG | GAGCA | GACGG |
| GCATG | CTCCA | GCATG | CCCGC |
| AGCCT | CTTTT | GCGGA | CGCTG |
| TCAAA | ATATC | TGCGT | GAATC |
| GTGGG | AGCAG | GCGCA | GGATT |
| GCGTA | TGGCG | CGGCG | AAAAC |
| AGGAC | AGCAT | GGATA | CACAT |
| AAAGC | ATGCG | GCGGC | CTCCT |
| TCTGA | GATAA | CATTC | GTTAT |
| ACATG | AGTAT | AGGCG | GCGTG |
| ATAAC | GAGTT | ATGAC | ATGCA |
| AAAAG | ACCAC | AATGC | GGGTG |
| TTGCG | GTCTT | TTCGG | TGTTT |
| GTCGG | TGGTT | ATGCG | ACGCT |
| GTTCG | CCCAT | TCTCT | TTTGA |
| AATTG | CGACG | TCAGG | GACTA |
| TAGTC | CTTAG | CGGTT | TGTCG |
| GAAAA | CCGTT | AAAAA | ACCAG |
| CAGAA | CCACC | AGATT | GATCT |
| GCTTC | ATCCC | AAACG | TCTGC |
| CTTTA | TGGTA | GTTAT | ATAGT |
| CCTGT | TCGCC | AAATG | CTCTG |
| TTCGG | GACTA | TGGGA | TTACC |
| GTGGT | TTGCG | GTGTC | ACGCA |
| GATAC | TTTTA | CACAT | ACTTT |
| TCGGT | GAAAA | ATCCC | GCAAA |
| AACGT | TTACA | CTATT | AGTAA |
| CAGAT | CAAAT | ACCTA | GGACT |
| CGTTC | ACCAT | ACACA | ATTCA |
| TTGAT | CTTTC | AAAAA | AAGGA |
| GTGTG | GAAAC | GGTGG | AAAAG |
| AAATT | AGAAG | AAGTA | AAGCA |
| ATTAT | TATTC | CGACT | TGAAA |
| ATGAT | ATCAG | AGAAA | CAACC |
| GACTC | ATTAC | GAAAC | ATTAA |
| CAAAA | GCATT | GATCA | GCTCG |
| ATAAA | TTCTC | ATATG | CAATG |
| AAAAT | TTCTT | AAAAA | GACTT |
| GGAAA | CAAGT | CTTTT | TTTTG |
| TGCAT | TTTTC | ACCCA | TTTCA |
| TGGAT | AAAGT | ATTAT | ACGAT |
| TGTTA | AAAAA | CGAAA | AACCT |
| GCTGT | CTTTC | ATCAC | CTGCA |
| TTTAG | TAAAA | TAGAA | TGGGA |
| GGGTG | AAGAC | AATTA | TTGAG |
| CAAAT | GTGTT | TAGAT | GCCGA |
| AACGA | TTAAA | GGGAA | GATGA |
| AGGAA | ATTGT | TGGGG | ATAAA |
| GTCGA | TAATC | TACAT | TTAGA |
| AGAGA | CTCTT | TTGAC | CTTCA |
| TTAAT | GAAAA | GAAGC | ACTTT |
| TCATT | CGGTG | TCCTT | GCTTT |
| CCAGC | ATTAT | GTTGC | TTTTA |
| AGGGT | ACACA | TTCCT | CGGAA |
| ATCAC | ACTAC | TGGCC | GCTGG |
| AATTG | AACTT | TTAAT | TTTAG |
| CTTTT | GATAT | TTTTG | ACGAT |
| ATTGA | AGATG | AAGAT | AACTT |
| TAATA | AGGCA | TGGAT | GCAAA |
| CTGAC | CATGC | TATAT | CCCTG |
| AATGC | GGCTA | CTTCT | CTGTA |
| TTCAA | TAAGC | CTGCA | AGCCA |
| TTTGT | GAGCT | TGAAT | CAAAC |
| AATCG | AT | | | where A, T, C and G represent adenine, thymine, cytosine and guanine, respectively.

The term "derivative sequences of the DNA base sequence" as used herein means derivative sequences of the aforesaid DNA base sequence in which the DNA base sequence has undergone base substitution, deletion, transposition and/or insertion without impairing its capability of increasing the amount of protein secreted by microorganisms.

The aforesaid DNA base sequence capable of increasing the amount of protein secreted by microorganisms (hereinafter referred to as "the DNA base sequence of the present invention") can be obtained by cloning from the chromosomal DNA of a microorganism having the ability to secrete protein or by chemical synthesis.

Preferred chromosomal DNA sources for obtaining the DNA base sequence of the present invention include chromosomal DNA possessed by Bacillus bacteria having the ability to secrete various types of proteins in considerable amounts, such as *Bacillus amyloliquefaciens* ATCC 23842* or ATCC 23350*; *Bacillus subtilis* ATCC e6051*; or *Bacillus licheniformis* ATCC 21415*.

*A stock strain maintained in the American Type Culture Collection, 12301 Parklawn Drive Rockville, MD 10852-1776, U.S.A.

By way of example, the procedure for obtaining the DNA base sequence of the present invention from a Bacillus bacterium will be described hereinbelow. First, DNA is isolated from cells of a Bacillus bacterium according to a conventional procedure. This DNA is fragmented either by means of a restriction enzyme or by a physical shearing action. It is to be understood that, if a restriction enzyme is used, it should be selected so as not to cleave the base sequence involved in the promotion of protein secretion. Even though the base sequence is inevitably cleaved by the restriction enzyme, care must be taken that the base sequence undergoes only partial degradation.

Then, the resulting DNA fragments are linked with plasmid DNA or phage DNA used as the vector. One example of an enzyme useful for this purpose is $T_4$ DNA ligase. Depending on the form of the DNA fragments to be linked, it may be desirable to use a linker according to the need. The hybrid DNA thus obtained may be introduced into a Bacillus bacterium according to any of the commonly used methods. By way of example, the hybrid DNA can be efficiently introduced into cells of a Bacillus bacterium by using the protoplast transformation method or the competent cell method. The use of a plasmid having a genetic marker (e.g., antibiotic resistance or the like) as the vector provides a very advantageous technique because the selection of transformed Bacillus bacteria can be facilitated by utilizing the genetic marker.

As the vector with which the chromosomal DNA fragments prepared from a Bacillus bacterium are linked, plasmids pTP4, pTP5 or pUB110 and phages $\phi$11, $\phi$105 or $\phi$1 are preferred. For example, the use of pUB110 permits the selection of transformants on the basis of kanamycin resistance, so that Bacillus bacteria having the plasmid introduced thereinto can be efficiently selected on a kanamycin-containing agar medium.

In the resulting large number of transformed Bacillus bacteria, recombinant plasmid DNAs including chromosomal DNA fragments having various molecular weights are present. Where transformation has been effected by using a plasmid as the vector, transformants having increased amounts of secreted protein are selected and cultured. Then, the cells are collected and plasmid DNA is extracted therefrom according to a conventional procedure. Thus, the DNA base sequence of the present invention is included in the extracted recombinant plasmid DNA. Transformants having increased amounts of secreted protein may be selected by culturing each transformant and examining whether or not the amount of protein secreted in the culture medium is increased as compared with the host bacterium. However, the selection can be facilitated by paying attention to a secreted protein having enzyme activity and detecting an increase in the enzyme activity of the enzyme protein secreted out of the cells. Such enzymes include, for example, amylase, protease, penicillinase, cellulase and alkaline phosphatase. Among these enzymes, protease is preferred as an index for the selection of transformants because its enzyme activity can be very easily determined by measuring the size of the haloes formed on a casein-containing agar plate or by enzymatic reaction using casein as the substrate.

Once a transformant having increased amounts of secreted protein has been obtained, the capability of its recombinant plasmid in increasing the amount of protein secreted by microorganisms can be confirmed by extracting plasmid DNA from its cells and introducing the extracted plasmid DNA again into the Bacillus bacterium used as the host. Where protease is selected as the secreted protein, it is possible to select a suitable transformant by taking an increase in extracellular protease activity as an index, extract recombinant plasmid DNA from its cells, and use the extracted recombinant plasmid DNA for purposes of transformation. If all of the transformants thus obtained shown an increase in extracellular protease activity, the extracted recombinant plasmid DNA is found to include a DNA base sequence capable of increasing the amount of protein secreted by microorganisms. Then, the restriction enzyme cleavage map of this recombinant plasmid DNA is made to characterize the contemplated recombinant plasmid and, on the basis of this cleavage map, the DNA base sequence of the inserted chromosomal DNA fragment derived from the Bacillus bacterium is determined, for example, by the Maxam-Gilbert method [Proc. Natl. Acad-Sci. U.S.A., 74,560(1977)]. The DNA base sequence of the present invention may be obtained as the whole or a part of the cloned DNA. If DNA capable of increasing the amount of protein secreted by microorganisms is cloned from mutant strains of the genus Bacillus or microorganisms of different genera or species, it is natural that there may be obtained DNA fragments comprising derivative sequences in which the DNA base sequence of the present invention has undergone mutational changes such as base substitution, deletion, insertion and/or transposition.

Moreover, microorganisms having very high amounts of secreted protein can be bred by incorporating the DNA base sequence of the present invention in the chromosomal DNA of a microorganism, particularly a bacterium of the genus Bacillus, or a vector and then introducing the resulting recombinant DNA into microorganisms. Thus, the DNA base sequence of the present invention has very wide applications in the microbial industry.

The present invention is further illustrated by the following example. However, this example is not to be construed to limit the scope of the invention.

EXAMPLE

Using 2 liters of the NB medium (containing 0.8% meat extract, 0.8% polypeptone and 0.4% NaCl and adjusted to pH 7.2), *Bacillus amyloliquefaciens* strain F (ATCC 23350) having high amounts of secretions of such proteins as amylase or protease was shake cultured at 37° C. The cells were collected in a late phase of logarithmic growth and chromosomal DNA was isolated therefrom according to Marmur's method [J. Mol. Biol., 3, 208 (1961)].

50 μg of this chromosomal DNA was treated with the restriction enzyme EcoRI by incubating it in 400 μl of a reaction mixture [containing 100 mM Tris-HCl (pH 7.5), 7 mM MgCl$_2$, 50 mM NaCl, 7 mM 2-mercaptoethanol, 0.01% bovine serum albumin and 20 units of EcoRI (manufactured by Takara Shuzo Co.)] at 37° C. for 3 hours. This reaction mixture was deprotenized with phenol and, thereafter, the degradation product was recovered by precipitation with ethanol.

Separately, 50 μg of pUB110 DNA, which is a plasmid capable of multiplying within the cells of a Bacillus bacterium, was treated in the same manner to obtain the complete degradation product of pUB110 DNA cleaved by EcoRI. Then, the resulting straight-chain DNA was treated with bacterial alkaline phosphatase (hereinafter referred to as "BAP") by incubating it in 300 μl of a reaction mixture [containing 50 mM Tris-HCl (pH 8.40 and 8 units of BAP (manufactured by Worthington Co.)] at 65° C. for 4 hours. This reaction mixture was deproteinized with phenol and, thereafter, the degradation product of DNA was recovered by precipitation with ethanol.

Using 0.03 unit of T$_4$ DNA ligase (manufactured by Takara Shuzo Co.), 0.5 μg of the above pUB110 DNA (EcoRI-cleaved, BAP-treated) and 1 μg of the above EcoRI degradation product of chromosomal DNA were linked together by incubating them in a reaction mixture [containing 66 mM Tris-HCl (pH 7.6), 6.6 mM MgCl$_2$, 10 mM dithiothreitol and 1 mA ATP] at 15° C. for 4 hours. Then, using the method of Chang et al. [Mol. Gen. Genet., 168, 111(1978)], the resulting recombinant plasmid was introduced into *Bacillus subtilis* strain 1A289 (aro1906 metB5 sacA321 amyE) having low protease-secreting ability (a stock strain maintained in the Bacillus Genetic Stock Center, the Ohio State University, Columbus, Ohio 4329, U.S.A.).

About 7,500 transformants having kanamycin resistance (Km[4]) induced by the introduction of the recombinant plasmid into *Bacillus subtilis* strain 1A289 were inoculated on an agar medium containing 0.6% casein and incubated at 37° C. for 18 hours. Thereafter, transformants having increased amounts of secreted protease were selected on the basis of their character of forming a large halo around the colony. One of these transformants having amounts of secreted protease was cultured in a kanamycin-containing medium. Then, recombinant plasmid DNA was extracted from its cells according to the method of Birnoboim et al. [Nucleic Acid Res., 7, 1513(1979)] and its restriction enzyme cleavage map was made. This plasmid was named pNP718 (see FIG. 1).

Using the aforesaid method of Chang et al., plasmid pNP718 was introduced into *Bacillus subtilis* strain 1A20 (dnaC ilvA1 met B5) having low amounts of secreted protease (a stock strain maintained in the Bacillus Genetic Stock Center, the Ohio State University, Columbus, Ohio 4329, U.S.A.). As a result, all of the resulting kanamycin-resistant transformants exhibited high amounts of secreted protease. Using the BY medium (containing 0.5% meat extract, 1% polypeptone, 0.2% yeast extract and 0.2% NaCl and adjusted to pH 7.2), *Bacillus subtilis* strain 1A20 used as the host and *Bacillus subtilis* strain 1A20 carrying pNP718 were shake cultured at 37° C. for 10 hours. Thereafter, each culture medium was filtered and the protease activity of the filtrate was determined. The results obtained by comparing the extracellular protease activities of these strains are shown in Table 1. In the determination of protease activity, neutral protease and alkaline protease activities were measured according to the method of Hagiwara et al. [J. Biochem., 45, 185(1958)] and expressed as relative values.

TABLE 1

| Strain | Extracellular protease activity (relative value) | |
|---|---|---|
| | Neutral protease | Alkaline protease |
| *Bacillus subtilis* 1A20 | 100 | 100 |
| *Bacillus subtilis* 1A20pNP718 | 1,040 | 450 |

Figure 2:
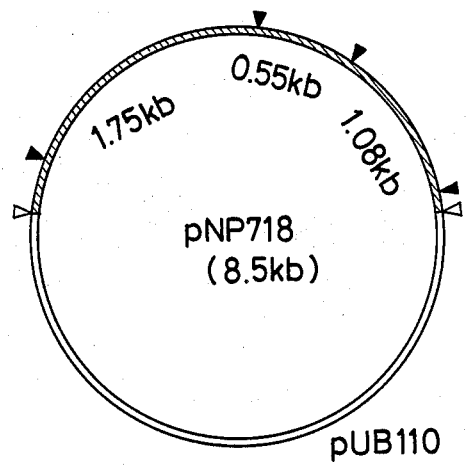
FIG. 2 is a restriction enzyme cleavage map of plasmid pNP181 showing the manner in which plasmid pNP181 is obtained from plasmid pNP718.
Figure 2:
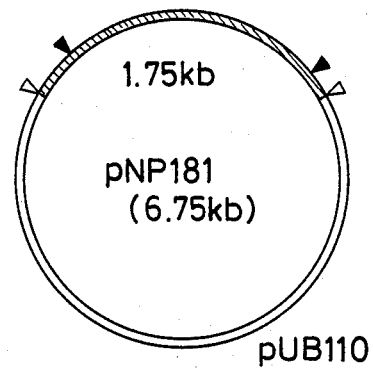

Plasmid pNP718 has four ClaI cleavage sites. Accordingly, the inventors obtained the partial degradation products of pNP718 cleaved by ClaI and recombined them by the use of T$_4$ DNA ligase to create a smaller recombinant plasmid including a gene involved in increasing the amount of protein secreted by microorganisms. This new recombinant plasmid will be described hereinbelow. Using the aforesaid method of Chang et al., the plasmid DNA (mixture) obtained by recombining the partial degradation products of pNP718 cleaved by ClaI was introduced into *Bacillus subtilis* strain 1A289. Then, using the aforesaid method of Birnoboim et al., plasmid DNA was extracted from some of the resulting transformants. Thus, there was obtained plasmid pNP181 having inserted therein a ClaI 1.75 kb fragment derived from pNP718 (see FIG. 2).

Using the method of Chang et al., this plasmid pNP181 was introduced again into Bacillus subtilis strain 1A289. When the amount of secreted protease of the resulting transformant MT-0181 (FERM BP-343) (a stock strain maintained in the Fermentation Research Institute Agency of Industrial Science and Technology, 1-3, Higashi 1 chome Yatabe-machi Tsukuba-gun, Ibaraki-ken 305, Japan) was determined by measuring the size of the haloes formed on the aforesaid casein-containing agar medium, it was confirmed that plasmid pNP181 was capable of increasing the amount of protease secretions of the bacterium.

Then, plasmid pNP181 was introduced into the aforesaid *Bacillus subtilis* strain 1A20 having low amount of secreted protease. The resulting transformant was examined for any increase in amount of secreted protease and the results thus obtained are shown in Table 2. The protease activity was determined in the same manner as for Table 1.

TABLE 2

| Strain | Extracellular protease activity (relative value) | |
|---|---|---|
| | Neutral protease | Alkaline protease |
| *Bacillus subtilis* 1A20 | 100 | 100 |
| *Bacillus subtilis* 1A20pNP181 | 700 | 420 |

The ability of this recombinant plasmid pNP181 to promote the secretion of neutral protease, alkaline protease and other proteins could also be confirmed by subjecting the proteins secreted in the culture medium of the transformant to polyacrylamide gel electrophoresis.

Figure 3:
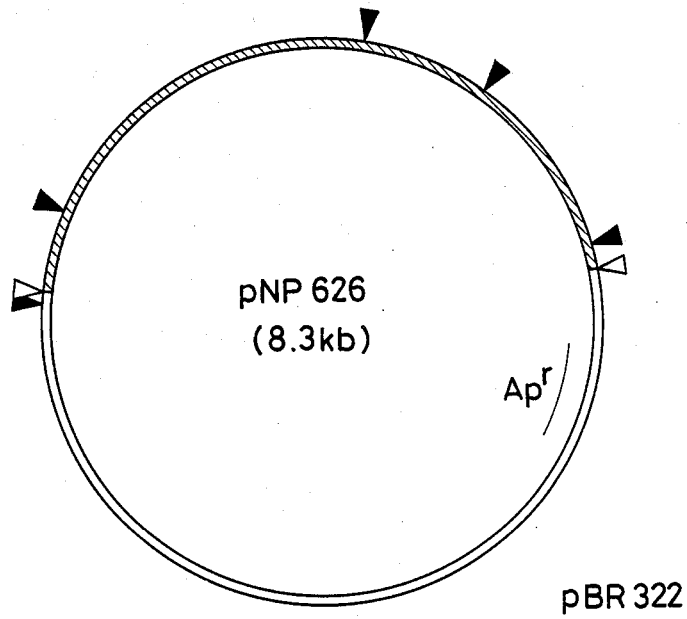
FIG. 3 is a restriction enzyme cleavage map of plasmid pNP626 in accordance with the present invention.

In order to determine the DNA base sequence of the ClaI 1.75 kb fragment, an EcoRI 4.0 kb fragment including the ClaI 1.75 kb fragment was cut out of plasmid pNP718 and linked with the EcoRI site of *Escherichia coli* vector pBR322 by means of T₄ DNA ligase to prepare recombinant plasmid pNP626 (see FIG. 3).

After plasmid pNP626 DNA was multiplied in *Escherichia coli* and its copy number was increased by means of chloramphenicol, plasmid DNA was extracted from the cells. The ClaI 1.75 kb fragment of the extracted plasmid DNA was further cleaved by the restriction enzymes HinfI, Sau3A, HpaII and TaqI to obtain smaller DNA fragments. The DNA base sequences of these smaller DNA fragments were determined according to the Maxam-Gilbert method [Proc. Natl. Acad. Sci. U.S.A., 74, 560(1977)].

In the ClaI 1.76 kb fragment, one of the strands was found to comprise the DNA base sequence claimed in claim 1. As shown in FIG. 4, this DNA base sequence includes base sequences (−35 region, TATA box) characteristic of the RNA synthesis initiation sites and base sequences (2 stem structures and a succeeding T-rich sequence) characteristic of the RNA synthesis termination sites. Thus, the presence of base sequences corresponding to the initiation sites, the termination sites and the regions located therebetween permits the expression of the character of increasing the amount of protein secretions of microorganisms. For this reason, the term "a part of said DNA base sequence" as used in claim 5 means at least one set of base sequences corresponding to an RNA synthesis initiation site, an RNA synthesis termination site and the region located therebetween, as shown in FIG. 4, or any combination of base sequences including such base sequences. In the recombinant plasmids pNP718, pNP181 and pNP626, the DNA base sequence claimed in claim 1 is included to result in the expression of the aforesaid character. Thus, it is to be understood that these recombinant plasmids fall within the scope of the recombinant plasmid claimed in claim 5.

What is claimed is:

1. A recombinant DNA plasmid, comprising: a sequence of bases capable of increasing protease secretion in *Bacillus subtilis*, wherein the sequence is:

| | | | |
|---|---|---|---|
| ATCGA | TACGC | TTCTC | CAGAG |
| AGAGC | TTGAG | GACAT | AGTCA |
| AAGAA | CTGCC | TTTAA | TTGAT |
| GAAGT | CGGAC | AGGCG | CTGCT |
| CGGTT | ATGAA | AACGA | TAATT |
| ACATG | ATGCT | CGGGC | TCGTC |
| AAAGC | CATTG | AATGC | AACAA |
| CTGGG | ACTGT | GACGA | GTGGG |
| GAAAA | GAACT | GGACA | AAGAA |
| GAAGC | ATATG | AATGT | TACTT |
| ACAGG | CGATC | GAATG | GTGCC |
| GGCAG | CTTAT | CGTGA | ATTGA |
| GGCGC | TTTAA | GCCGA | CCACC |
| TGAGG | GCGAT | GATGA | ACCGG |
| CTTTG | CTCTC | TGAAC | AGACT |
| GACAC | GGATG | CCGTC | GGGAT |
| TAAAT | GTCAC | ATCAA | AATCA |
| TTTTT | GATGC | CGGTC | TGCTT |
| AATGA | GCCGC | TTGAC | CGCCG |
| CGGCG | TCAGA | TGATT | GCGCT |
| GCGGT | GAGGA | TGCGG | CGCGC |
| AAGCT | CTTTT | GACGC | CGACA |
| GCCGC | GCAAG | GAGCA | GACGG |
| GCGTC | CTCCA | GCATG | CCCGC |
| AGCCT | CTTTT | GCGGA | CGCTG |
| TCAAA | ATATC | TGCGT | GAATC |
| GTGGG | AGCAG | GCGCA | GGATT |
| CGCTA | TGGCG | CGGCG | AAAAC |
| AGGAC | AGCAT | GGATA | CACAT |
| AAAGC | ATGCG | GCGGC | CTCCT |
| TCTGA | GATAA | CATTC | GTTAT |
| ACATG | AGTAT | AGGCG | GCGTG |
| ATAAC | GAGTT | ATGAC | ATGCA |
| AAAAG | ACCAC | AATGC | GGGTG |
| TTGCG | GTCTT | TTCGG | TGTTT |
| GTCGG | TGGTT | ATGCG | ACGCT |
| GTTCT | CCCAT | TCTCT | TTTGA |
| AATTG | CGACG | TCAGG | GACTA |
| TAGTC | CTTAG | CGGTT | TGTCG |
| GAAAA | CCGTT | AAAAA | ACCAG |
| CAGAA | CCACC | AGATT | GATCT |
| GCTTC | ATCCC | AAACG | TCTGC |
| CTTTA | TGGTA | GTTAT | ATAGT |
| CCTGT | TCGCC | AAATG | CTCTG |
| TTCGG | GACTA | TGGGA | TTACC |
| GTGGT | TTGCG | GTGTC | ACGCA |
| GATAC | TTTTA | CACAT | ACTTT |
| TCGGT | GAAAA | ATCCC | GCAAA |
| AACGT | TTACA | CTATT | AGTAA |
| CAGAT | CAAAT | ACCTA | GGACT |
| CGTTC | ACCAT | ACACA | ATTCA |
| TTGAT | CTTTC | AAAAA | AAGGA |
| GTGTG | GAAAC | GGTGG | AAAAG |
| AAATT | AGAAG | AAGTA | AAGCA |
| ATTAT | TATTC | CGACT | TGAAA |
| ATGAT | ATCAG | AGAAA | CAACC |
| GACTC | ATTAC | GAAAC | ATTAA |
| CAAAA | GCATT | GATCA | GCTCG |
| ATAAA | TTCTC | ATATG | CAATG |
| AAAAT | TTCTT | AAAAA | GACTT |
| GGAAA | CAAGT | CTTTT | TTTTG |
| TGCAT | TTTTC | ACCCA | TTTCA |
| TGGAT | AAAGT | ATTAT | ACGAT |
| TGTTA | AAAAA | CGAAA | AACCT |
| GCTGT | CTTTC | ATCAC | CTGCA |
| TTTAG | TAAAA | TAGAA | TGGGA |
| GGGTG | AAGAC | AATTA | TTGAG |
| CAAAT | GTGTT | TAGAT | GCCGA |
| AACGA | TTAAA | GGGAA | GATGA |
| AGGAA | ATTGT | TGGGG | ATAAA |
| GTCGA | TAATC | TACAT | TTAGA |
| AGAGA | CTCTT | TTGAC | CTTCA |
| TTAAT | GAAAA | GAAGC | ACTTT |
| TCATT | CGGTG | TCCTT | GCTTT |
| CCAGC | ATTAT | GTTGC | TTTTA |
| AGGGT | ACACA | TTCCT | CGGAA |
| ATCAC | ACTAC | TGGCC | GCTGG |
| AATTG | AACTT | TTAAT | TTTAG |
| CTTTT | GATAT | TTTTG | ACGAT |
| ATTGA | AGATG | AAGAT | AACTT |
| TAATA | AGGCA | TGGAT | GCAAA |
| CTGAC | CATGC | TATAT | CCCTG |
| AATGC | GGCTA | CTTCT | CTGTA |
| TTCAA | TAAGC | CTGCA | AGCCA |
| TTTGT | GAGCT | TGAAT | CAAAC |
| AATCG | AT | | | where A, T, C and G represent adenine, thymine, cytosine and guanine, respectively.

2. A recombinant DNA plasmid comprising a derivative sequence derived from the sequence of bases of claim 1, wherein the derivative results from base substitution, base deletion, base transposition or base insertion, and wherein the derivative is capable of increasing protease secretion in Bacillus subtilis.

3. The plasmid of claim 1 wherein the base sequence is derived from the chromosomal DNA of a bacterium of the genus Bacillus.

4. The plasmid of claim 3 wherein the bacterium is selected from the group consisting of *Bacillus amyloliquefaciens* ATCC 23350, *Bacillus subtilis*, and *Bacillus licheniformis*.

5. A recombinant DNA plasmid, comprising: a plasmid selected from the group consisting of pNP718, pNP181 and pNP626.

6. A method for preparing DNA plasmids capable of increasing protease secretion in Bacillus subtilis, comprising the steps of:
   (a) growing a culture of Bacillus amyloliguefaciens which secretes protease; and
   (b) isolating chromosomal DNA from said culture of Bacillus amyloliguefaciens; and
   (c) treating the chromosomal DNA with restriction enzyme EcoRI to obtain a DNA fragment comprising a sequence of bases capable of increasing protease secretion in Bacillus subtilis; and
   (d) treating pUB110, a plasmid capable of growing within Bacillus, with restriction enzyme EcoRI to obtain a linear puB110; and
   (e) treating the linear pUB110 with bacterial alkaline phosphatase; and
   (f) linking the DNA fragment obtained in step (c) and the linear pUB110 obtained in step (e) together with T4 ligase, to obtain a recombinant DNA plasmid capable of enhancing protease secretion in Bacillus subtilis.

7. A method of using DNA plasmids capable of enhancing protease secretion in *Bacillus subtilis,* comprising the step of:
   introducing a recombinant DNA plasmid into Bacillus subtilis, wherein the plasmid has the DNA base sequence of

| | | | |
|---|---|---|---|
| ATCGA | TACGC | TTCTC | CAGAG |
| AGAGC | TTGAG | GACAT | AGTCA |
| AAGAA | CTGCC | TTTAA | TTGAT |
| GAAGT | CGGAC | AGGCG | CTGCT |
| CGGTT | ATGAA | AACGA | TTATT |
| ACATG | ATGCT | CGGGC | TCGTC |
| AAAGC | CATTG | AATGC | AACAA |
| CTGGG | ACTGT | GACGA | GTGGG |
| GAAAA | GAACT | GGACA | AAGAA |
| GAAGC | ATATG | AATGT | TACTT |
| ACAGG | CGATC | GAATG | GTGCC |
| GGCAG | CTTAT | CGTGA | ATTGA |
| GGCGC | TTTAA | GCCGA | CCACC |
| TGAGG | GCGAT | GATGA | ACCGG |
| CTTTG | CTCTC | TGAAC | AGACT |
| GACAC | GGATG | CCGTC | GGGAT |
| TAAAT | GTCAC | ATCAA | AATCA |
| TTTTT | GATGC | CGGTC | TGCTT |
| AATGA | GCCGC | TTGAC | CGCCG |
| CGGCG | TCAGA | TGATT | GCGCT |
| GCGGT | GAGGA | TGCGG | CGCGC |
| AAGCT | CTTTT | GACGC | CGACA |
| GCCGC | GCAAG | GAGCA | GACGG |
| GCGTC | CTCCA | GCATG | CCCGC |
| AGCCT | CTTTT | GCGGA | CGCTG |
| TCAAA | ATATC | TGCGT | GAATC |
| GTGGG | AGCAG | GCGCA | GGATT |
| CGCTA | TGGCG | CGGCG | AAAAC |
| AGGAC | AGCAT | GGATA | CACAT |
| AAAGC | ATGCG | GCGGC | CTCCT |
| TCTGA | GATAA | CATTC | GTTAT |
| ACATG | AGTAT | AGGCG | GCGTG |
| ATAAC | GAGTT | ATGAC | ATGCA |
| AAAAG | ACCAC | AATGC | GGGTG |
| TTGCG | GTCTT | TTCGG | TGTTT |
| GTCGG | TGGTT | ATGCG | ACGCT |
| GTTCT | CCCAT | TCTCT | TTTGA |
| AATTG | CGACG | TCAGG | GACTA |
| TAGTC | CTTAG | CGGTT | TGTCG |
| GAAAA | CCGTT | AAAAA | ACCAG |
| CAGAA | CCACC | AGATT | GATCT |
| GCTTC | ATCCC | AAACG | TCTGC |
| CTTTA | TGGTA | GTTAT | ATAGT |
| CCTGT | TCGCC | AAATG | CTCTG |
| TTCGG | GACTA | TGGGA | TTACC |
| GTGGT | TTGCG | GTGTC | ACGCA |
| GATAC | TTTTA | CACAT | ACTTT |
| TCGGT | GAAAA | ATCCC | GCAAA |
| AACGT | TTACA | CTATT | AGTAA |
| CAGAT | CAAAT | ACCTA | GGACT |
| CGTTC | ACCAT | ACACA | ATTCA |
| TTGAT | CTTTC | AAAAA | AAGGA |
| GTGTG | GAAAC | GGTGG | AAAAG |
| AAATT | AGAAG | AAGTA | AAGCA |
| ATTAT | TATTC | CGACT | TGAAA |
| ATGAT | ATCAG | AGAAA | CAACC |
| GACTC | ATTAC | GAAAC | ATTAA |
| CAAAA | GCATT | GATCA | GCTCG |
| ATAAA | TTCTC | ATATG | CAATG |
| AAAAT | TTCTT | AAAAA | GACTT |
| GGAAA | CAAGT | CTTTT | TTTTG |
| TGCAT | TTTTC | ACCCA | TTTCA |
| TGGAT | AAAGT | ATTAT | ACGAT |
| TGTTA | AAAAA | CGAAA | AACCT |
| GCTGT | CTTTC | ATCAC | CTGCA |
| TTTAG | TAAAA | TAGAA | TGGGA |
| GGGTG | AAGAC | AATTA | TTGAG |
| CAAAT | GTGTT | TAGAT | GCCGA |
| AACGA | TTAAA | GGGAA | GATGA |
| AGGAA | ATTGT | TGGGG | ATAAA |
| GTCGA | TAATC | TACAT | TTAGA |
| AGAGA | CTCTT | TTGAC | CTTCA |
| TTAAT | GAAAA | GAAGC | ACTTT |
| TCATT | CGGTG | TCCTT | GCTTT |
| CCAGC | ATTAT | GTTGC | TTTTA |
| AGGGT | ACACA | TTCCT | CGGAA |
| ATCAC | ACTAC | TGGCC | GCTGG |
| AATTG | AACTT | TTAAT | TTTAG |
| CTTTT | GATAT | TTTTG | ACGAT |
| ATTGA | AGATG | AAGAT | AACTT |
| TAATA | AGGCA | TGGAT | GCAAA |
| CTGAC | CATGC | TATAT | CCCTG |
| AATGC | GGCTA | CTTCT | CTGTA |
| TTCAA | TAAGC | CTGCA | AGCCA |
| TTTGT | GAGCT | TGAAT | CAAAC |
| AATCG | AT | | | where A, T, C and G represent adenine, thymine, cytosine and guanine, respectively.

* * * * *